United States Patent
Dianis et al.

(10) Patent No.: US 11,284,910 B2
(45) Date of Patent: Mar. 29, 2022

(54) INTERLEAVED BEAM PATTERN FOR SONOTHHROMBOLYSIS AND OTHER VASCULAR ACOUSTIC RESONATOR MEDIATED THERAPIES

(71) Applicants: KONINKLIJKE PHILIPS N.V., Eindhoven (NL); BRACCO SUISSE SA, Manno (CH)

(72) Inventors: Scott William Dianis, Andover, MA (US); Jeffry Earl Powers, Bainbridge Island, WA (US); Ralf Seip, Carmel, NY (US); William Tao Shi, Cambridge, MA (US); Yannick Bohren, Plan Les Ouates (CH); Emmanuel Jean-Marie Gaud, La Croix-de-Rozon (CH); Jean-Marc Paul Robert Hyvelin, Geneva (CH)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 877 days.

(21) Appl. No.: 15/780,248

(22) PCT Filed: Dec. 7, 2016

(86) PCT No.: PCT/EP2016/080127
§ 371 (c)(1),
(2) Date: May 31, 2018

(87) PCT Pub. No.: WO2017/097853
PCT Pub. Date: Jun. 15, 2017

(65) Prior Publication Data
US 2018/0353777 A1    Dec. 13, 2018

Related U.S. Application Data

(60) Provisional application No. 62/265,154, filed on Dec. 9, 2015.

(30) Foreign Application Priority Data

Feb. 11, 2016   (EP) .................................. 16155298

(51) Int. Cl.
A61B 17/22    (2006.01)
A61B 8/06     (2006.01)
(Continued)

(52) U.S. Cl.
CPC .......... *A61B 17/22004* (2013.01); *A61B 8/06* (2013.01); *A61B 8/14* (2013.01);
(Continued)

(58) Field of Classification Search
CPC ....... A61B 8/06; A61B 8/14; A61B 17/22004; A61B 2017/00106; A61B 2017/22008;
(Continued)

(56) References Cited

U.S. PATENT DOCUMENTS 5,556,610 A    9/1996  Yan et al.
5,686,060 A    11/1997 Schneider et al.
(Continued)

FOREIGN PATENT DOCUMENTS

WO    9115244 A2   10/1991
WO    03070105 A1  8/2003
(Continued)

OTHER PUBLICATIONS

Collis et al "Cavitation microstreaming and stress fields created by microbubbles" Ultrasonics 50, (2010) p. 273-279.

*Primary Examiner* — Amelie R Davis
*Assistant Examiner* — Helene Bor

(57) ABSTRACT

A therapeutic ultrasound system transmits a staggered or interleaved pattern of therapy beams for use in sonothrombolysis and other Vascular Acoustic Resonators (VAR) mediated therapy. The inventive technique minimizes VAR,
(Continued)

e.g. microbubble, destruction due to adjacent beams, ensures uniform sonication of the targeted region by filling in the spaces between the beams in subsequent passes, and further provides a means for bubble replenishment to maximize the clot lysis from ultrasound. The technique is also applicable to diagnostic ultrasound, VAR mediated drug delivery and blood brain barrier opening.

16 Claims, 6 Drawing Sheets

(51) Int. Cl.
    *A61B 8/14*     (2006.01)
    *A61B 8/08*     (2006.01)
    *A61B 17/00*     (2006.01)

(52) U.S. Cl.
    CPC ..... *A61B 8/488* (2013.01); *A61B 2017/00106* (2013.01); *A61B 2017/22008* (2013.01); *A61B 2017/22028* (2013.01)

(58) Field of Classification Search
    CPC ............ A61B 2017/22028; A61N 7/02; A61N 2007/0039; A61N 2007/0052; A61N 2007/0078; A61N 2007/0082; A61N 2007/0095; A61N 2007/027
    See application file for complete search history.

(56) References Cited

U.S. PATENT DOCUMENTS

| | | |
|---|---|---|
| 5,711,933 A | 1/1998 | Bichon et al. |
| 5,997,479 A | 12/1999 | Savord |
| 6,013,032 A | 1/2000 | Savord |
| 6,071,239 A | 6/2000 | Cribbs et al. |
| 6,333,021 B1 | 12/2001 | Schneider et al. |
| 6,530,885 B1 | 3/2003 | Entrekin et al. |
| 6,623,432 B2 | 9/2003 | Powers et al. |
| 6,723,050 B2 | 4/2004 | Dow et al. |
| 6,881,397 B2 | 4/2005 | Schneider et al. |
| 8,211,023 B2 | 7/2012 | Swan et al. |
| 2005/0085748 A1 | 4/2005 | Culp et al. |
| 2007/0055156 A1* | 3/2007 | Desilets ............... A61B 8/0858 600/439 |
| 2008/0097206 A1* | 4/2008 | Chomas .................. A61N 7/00 600/439 |
| 2008/0262350 A1 | 10/2008 | Unger |
| 2008/0269608 A1* | 10/2008 | Anderson ............... A61N 7/02 600/439 |
| 2010/0016707 A1* | 1/2010 | Amara ................. A61B 8/0816 600/411 |
| 2010/0056924 A1* | 3/2010 | Powers .................. A61B 8/481 600/458 |
| 2010/0160781 A1* | 6/2010 | Carter ..................... A61B 8/06 600/439 |
| 2010/0312150 A1 | 12/2010 | Mast et al. |
| 2012/0029353 A1* | 2/2012 | Slayton ............... A61B 8/4254 600/439 |
| 2012/0130288 A1 | 5/2012 | Holland et al. |
| 2014/0316306 A1* | 10/2014 | Slayton .................. A61N 7/02 601/2 |

FOREIGN PATENT DOCUMENTS

| | | |
|---|---|---|
| WO | 2004069284 A2 | 9/2004 |
| WO | 2005074805 A1 | 8/2005 |
| WO | 2007129166 A2 | 11/2007 |
| WO | 2015000953 A1 | 1/2015 |

\* cited by examiner replenishment period → replenishment period → replenishment period →

| | | | | | | |
|---|---|---|---|---|---|---|
|1|3|1|3|1|3|1|
|4|2|4|2|4|2|4|
|1|3|1|3|1|3|1|
|4|2|4|2|4|2|4|
|1|3|1|3|1|3|1|

FIG. 6

| | | | | | | |
|---|---|---|---|---|---|---|
|1|3|2|1|3|2|1|
|3|2|1|3|2|1|3|
|1|3|2|1|3|2|1|
|3|2|1|3|2|1|3|
|1|3|2|1|3|2|1|

FIG. 7

| | | | | | |
|---|---|---|---|---|---|
|1|2|1|2|1|2|
|3|4|3|4|3|4|
|1|2|1|2|1|2|
|3|4|3|4|3|4|
|1|2|1|2|1|2|
|3|4|3|4|3|4|

FIG. 8

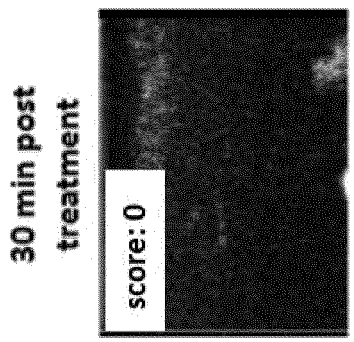
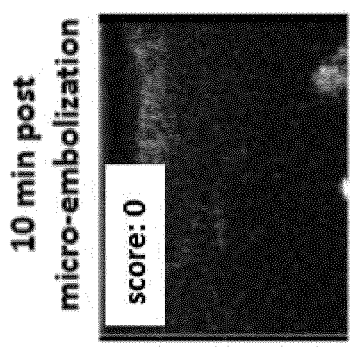
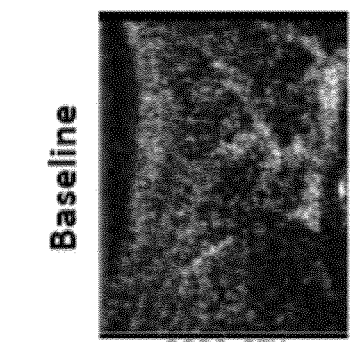
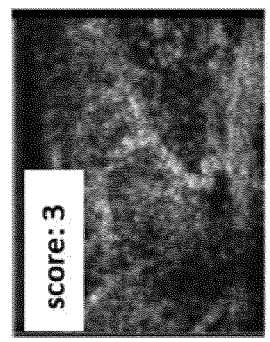
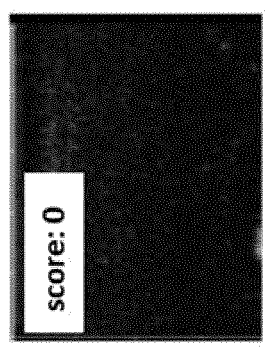
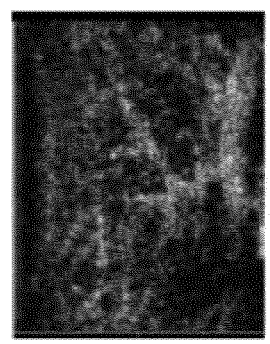
FIG. 9a(1) FIG. 9a(2) FIG. 9a(3) FIG. 9b(1) FIG. 9b(2) FIG. 9b(3)

INTERLEAVED BEAM PATTERN FOR SONOTHHROMBOLYSIS AND OTHER VASCULAR ACOUSTIC RESONATOR MEDIATED THERAPIES

This application is the U.S. National Phase application under 35 U.S.C. § 371 of International Application No. PCT/EP2016/080127, filed on Dec. 7, 2016, which claims the benefit of Provisional Application Ser. No. 62/265,154, filed Dec. 9, 2015 and EP Application Serial No. 16155298.9 filed Feb. 11, 2016. These applications are hereby incorporated by reference herein.

FIELD OF THE INVENTION

This disclosure relates to medical ultrasound systems and, in particular, to ultrasound systems which perform sonothrombolysis and other therapy in combination with vascular acoustic resonators (VARs), such as gas-filled microvesicles.

BACKGROUND OF THE INVENTION

Ischemic stroke is one of the most debilitating disorders known to medicine. The blockage or significant reduction of the flow of blood to the brain can rapidly result in paralysis or death. Attempts to achieve recanalization through thrombolytic drug therapy such as treatment with tissue plasminogen activator (tPA) has been reported to cause symptomatic intracerebral hemorrhage in a number of cases. Advances in the diagnosis and treatment of this crippling affliction are the subject of continuing medical research.

U.S. Pat. No. 8,211,023 (Swan et al.) describes a diagnostic ultrasound system and method which enable a clinician to transcranially visualize a region of the cerebral vasculature where blood clots may be present. Either two dimensional or three dimensional imaging may be employed. The imaging of the vasculature is preferably enhanced by the administration of VARs. If the flow conditions of the vasculature indicate the presence of a partial or complete occlusion from a blood clot, a focused or pencil beam of ultrasound is directed to the location of the blockage to break up the clot by the vibrations and/or rupturing of the VARs. In some instances the ruptured VARs may also release an encapsulated thrombolytic drug. The patent also describes monitoring the cranial vasculature by ultrasonic imaging for changes which are indicative of the recurrence of an occlusion so that medical aid can be alerted to the recurrent condition.

In order for the ultrasound to effectively break up or lyse a blood clot, it is important for the ultrasound to uniformly and completely insonify the location of the clot-induced blood flow arrest or reduction, and to effectively use the VARs at the locus of the clot and the relevant region of interest surrounding it to break up the clot as rapidly and thoroughly as possible. The region of interest may be as small as the clot, i.e. when clearly identified or of several cubic centimeters when clot is suspected but not clearly identifiable or localizable. In order to achieve sufficient ultrasound amplitude for the desired therapeutic effect, application of focused ultrasound is generally preferred. However, because of the relatively small surface area of focused ultrasound beam, the focused beam must be steered throughout the region of interest for adequate clot treatment. Focused ultrasound beam area is characterized by a peak beam pressure and a beam width at which the lateral pressure is half the peak beam. Therefore, VARs are subjected to different ultrasound pressure according to their location with regards to the peak pressure of the ultrasound beam pattern. At low to modest acoustic pressure of 50-100 kPA, VARs gradually disappear due to gradual escape of the gas from the VAR's envelope. But when VARs are exposed to sufficient acoustic pressure amplitude to have a therapeutic effect, typically 200-400 kPa, VARs envelope is destroyed rapidly but remain active for sonothrombolysis (typically for several tens of milliseconds) as long as they continue to remain in the ultrasound field. As a consequence, for sufficient acoustic beam pressure VARs will be efficient at the beam peak, but VARs near the beam will disappear gradually. This disappearance of VARs away from the center of a beam area occurs at lower ultrasound amplitudes which do not effectively contribute to the therapeutic effect. Accordingly it is desirable to limit or prevent such disappearance (or ineffective destruction) of VARs, so that the clot lysis will occur as rapidly and effectively as possible.

It is an object of the present disclosure to improve the effectiveness of sonothrombolysis through more effective use of the VARs at the site of a blood clot. It is a further object of the disclosure to allow the replenishment of VARs which are ineffectively destroyed adjacent to the lysing beam center.

In some aspects, the present disclosure includes methods and systems for insonifying a region of interest, e.g., a therapy region. For example, the present disclosure includes methods and systems for insonifying a therapy region containing VARs with ultrasound therapy beams. The methods can include and the systems can be configured for transmitting a first pattern of ultrasound therapy beams through the therapy region, the beams being separated from each other by a predetermined spacing between the beams, and transmitting a second pattern of ultrasound therapy beams through the therapy region, the beams being directed to the spaces which separate the beams of the first beam pattern from each other. According to an aspect, the spacing between the beams of the first (and preferably subsequent patterns) leaves residual VARs between the beams.

In certain aspects, the methods can include and the systems can be configured for refraining from transmitting during a time interval between the different patterns, e.g., between each pattern to allow VAR replenishment at the therapy region. The time intervals can include a predetermined amount of time ranging, e.g. at least greater than 0.1 seconds, from 0.1 to 20 seconds, from 0.5 to 10 seconds, from 1 to 2 seconds, and from 1 to 5 seconds.

The methods can include and the systems can be configured for transmitting other patterns, such as transmitting third and fourth patterns of ultrasound therapy beams having the same beam patterns as the first and second beam patterns and being offset by an interbeam spacing between the ultrasound therapy beams. Transmitting of the third and fourth patterns of ultrasound therapy beams can further include transmitting a third beam pattern of the same pattern as the second beam pattern, and transmitting a fourth beam pattern of the same pattern as the first beam pattern, the ultrasound therapy beams being offset by an interbeam spacing.

In general each beam is characterized by a peak beam pressure (and power) and by respective beam widths at which the corresponding lateral pressure is a percentage of the peak beam pressure or power. For instance, beam widths can be identified as having a lateral pressure of 18.25-25% or half (50%) of the peak beam pressure, referred herein as a half pressure beam width; also, beam widths can be identified as having a lateral pressure of about 70% of the peak beam pressure, which also corresponds in general to the beam width at half power peak beam, referred herein as a half power beam width. In certain aspects, transmitting a pattern of ultrasound therapy beams can include transmitting beams where the respective beam centers are separated from each other by a spacing which is at least equal to the half power peak beam width (corresponding to a beam width at about 70% of peak beam pressure). In other aspects, transmitting a pattern of ultrasound therapy beams can include transmitting beams separated from each other by a spacing which is at least equal to half (50%) pressure beam width. In some aspects, transmitting a pattern of ultrasound therapy beams can include transmitting beams separated from each other by a spacing which is not greater than the 18.75%-25% pressure beam width. The transmitting of a pattern of ultrasound therapy beams can include transmitting beams separated from each other by a spacing, which, e.g., can in certain embodiments range from 2.6 to 5.2 mm.

In certain aspects, transmitting a first pattern of ultrasound therapy beams can include transmitting a pattern of beams which are separated from each other horizontally and vertically. The transmitting a second pattern of ultrasound therapy beams can also include transmitting a pattern of beams which are spatially interleaved horizontally and vertically between the beams of the first pattern, and transmitting a third pattern of ultrasound therapy beams which are spatially interleaved horizontally and vertically between the beams of the first and second patterns.

In certain aspects, the methods can include and systems can be configured for transmitting a first pattern of ultrasound therapy beams in which beams are separated from each other horizontally and vertically. The methods can include and systems can be configured for transmitting a second pattern of ultrasound therapy beams in which beams are spatially interleaved diagonally between the beams of the first pattern. Also, the methods can include and systems can be configured for transmitting a third pattern of ultrasound therapy beams which are spatially interleaved horizontally and vertically between the beams of the first and second patterns, and transmitting a fourth pattern of ultrasound therapy beams which are spatially interleaved horizontally and vertically between the beams of the first and second patterns.

In some aspects, the present disclosure can include ultrasound systems for insonifying a therapy region and configured to carry out the methods disclosed herein. For instance, the present disclosure can include an ultrasound system having instructions thereon, which when executed, cause the system to transmit a first pattern of ultrasound therapy beams through a therapy region, the beam areas being separated from each other by a predetermined spacing, which under some circumstances can leave residual VARs between the beams, and transmit a second pattern of ultrasound therapy beams through the therapy region, the beams being directed to the spaces which separate the beams of the first beam pattern from each other. In other embodiments, the present disclosure can include a region containing VARs with spatially interleaved patterns of ultrasound beams. The system can include a two dimensional (2D) array (for example, a phased 2D array) of ultrasonic transducer elements, and a transmit controller coupled to the transducer array to electronically steer therapy beams into the therapeutic region. The transmit controller can be configured to cause the transducer array to (1) transmit a first pattern of ultrasound therapy beams through the therapy region, the beams being separated from each other by predetermined spaces and (2) transmit a second pattern of ultrasound therapy beams directed to the spaces separating the beams of the first beam pattern from each other. In particular the predetermined spaces between the beams of a pattern are such that the lateral beam lower ultrasound pressure would leave a certain amount of the VARs which are within said spaces substantially unaffected. In certain aspects, the transmit controller can be configured to cause the transducer array to refrain from transmitting for a refresh interval between transmission of the first and second pattern. The transmit controller can also be configured to cause the transducer array to transmit a third pattern of ultrasound therapy beams which are spatially interleaved between the beams of the first and second beam patterns, and/or to cause the transducer array to transmit a fourth pattern of ultrasound therapy beams which are spatially interleaved between the beams of the first and second beam patterns.

BRIEF DESCRIPTION OF THE DRAWINGS

FIG. 6 is a numerical representation of another four-pattern therapy beam sequence in accordance with the principles of the present disclosure.

FIG. 7 is a numerical representation of a three-pattern therapy beam sequence in accordance with the principles of the present disclosure.

FIG. 8 is a numerical representation of another four-pattern lysing beam sequence in accordance with the principles of the present disclosure.

FIGS. 9a to 9b illustrate experimental results conducted on rats.

SUMMARY OF THE INVENTION

In accordance with the principles of the present disclosure, sonothrombolysis systems and methods are described which make more efficient use of vascular acoustic resonators VARs at the site of a blood clot through interleaved therapy beam scanning. The sonothrombolysis system comprises at least one ultrasound array (for example, phased array) arranged to transmit ultrasound therapy beams into a region of interest; and a transmit controller coupled to the array and arranged to control steering of the therapy beams in a plurality of sequential patterns, wherein each subsequent in time pattern comprises of beam areas which are spatially interleaved between beam areas of the previous pattern.

A limited overlap between the beam areas of the subsequent patterns reduces the instantaneous acoustic power at the skin's surface, while providing a sufficient acoustic power for VAR destruction at the desired location below said surface. The residual VARs, optionally combined with further VARs deriving from replenishment, can then be effectively destroyed by subsequent scanning with a different beam pattern. For example, two or more different scanning patterns of therapy beams can be alternately applied with predetermined beam spacing (which would typically leave residual VARs between the beams of a respective pattern). The residual VARs, optionally combined with further VARs deriving from replenishment, can then be effectively destroyed by subsequent scanning with a different beam pattern. A time interval or refresh interval between the scanning of each pattern is generally preferred as it may aid in allowing the replenishment of VARs for a more effective application of the subsequent beam pattern. The present disclosure is effective, for example, in sonothrombolysis treatment for stroke. In such instances, insonifying the entire brain is an option, but transmitting high levels of ultrasound energy through a small temporal bone window can cause surface burns to the patient. As such, to get sufficient amplitude for VAR destruction at the desired location, the ultrasound beam configurations described herein can be configured and focused to reduce the instantaneous power at the skin's surface, but increase the amplitude at the location of interest through focusing gain. It is further noted that the present disclosure is equally applicable to cardiac applications or other applications where the interaction between the ultrasound exposure and circulating VARs needs to be maximized by minimizing unintended VAR destruction, such as in ultrasound-mediated drug or gene delivery or opening the blood brain barrier.

Figure 1:
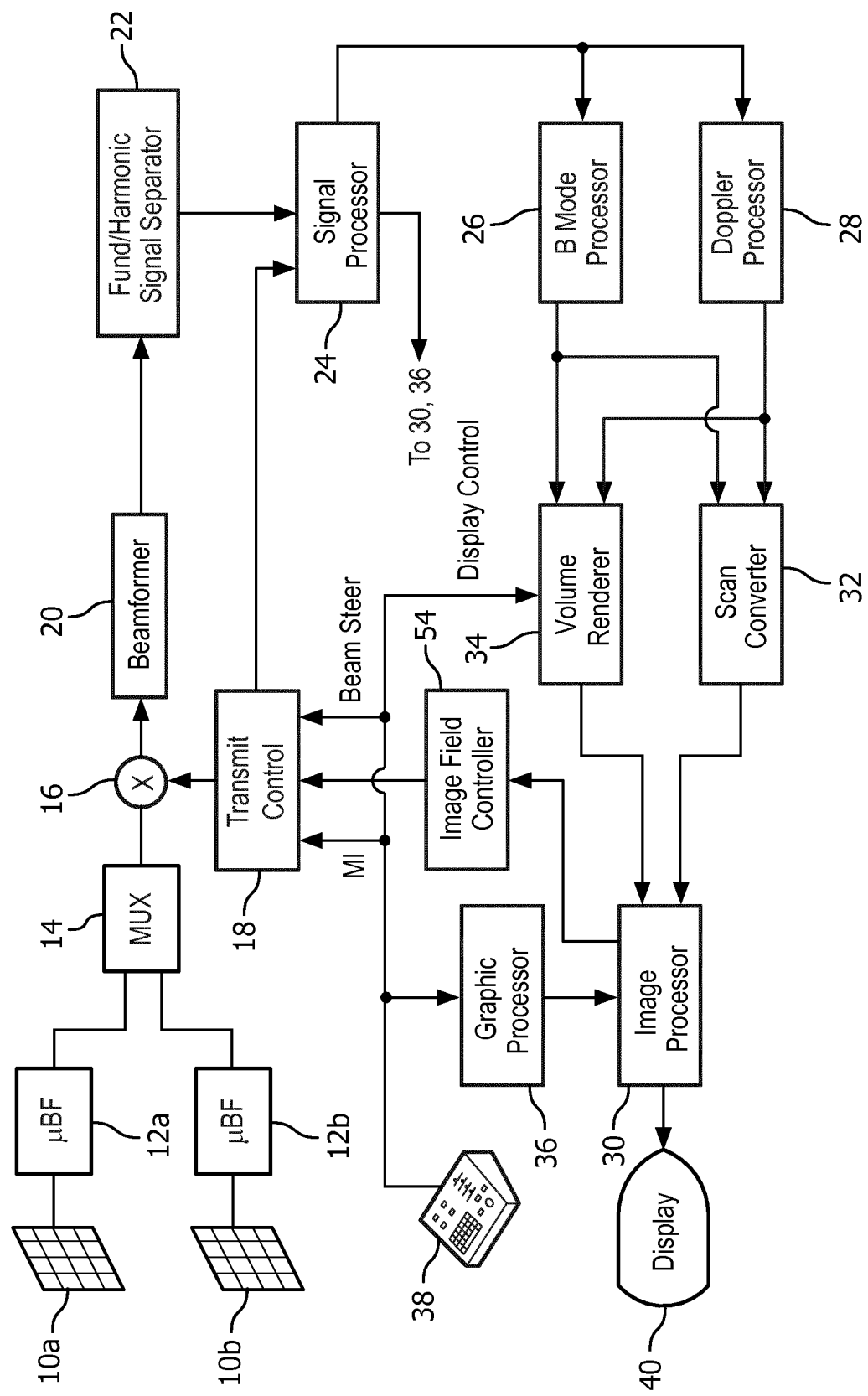
FIG. 1 illustrates in block diagram form an ultrasonic system constructed in accordance with the principles of the present disclosure.

Referring first to FIG. 1, an ultrasound system constructed in accordance with the principles of the present disclosure is shown in block diagram form. Two transducer arrays 10a and 10b are provided for transmitting ultrasonic waves and receiving echo information. In this example the arrays shown are two dimensional arrays of transducer elements (matrix arrays) capable of scanning a volumetric region and providing 3D image information for imaging. In some embodiments, the array of transducer elements can be coupled to a system beamformer depending on the element count. For higher element counts, the transducer arrays can be coupled to microbeamformers 12a and 12b which control transmission and reception of signals by the array elements. Microbeamformers are also capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) Signals are routed to and from the microbeamformers by a multiplexer 14 by time-interleaving signals. The multiplexer is coupled to a transmit/receive (T/R) switch 16 which switches between transmission and reception and protects the main beamformer 20 from high energy transmit signals. The transmission of ultrasonic beams from the transducer arrays 10a and 10b under control of the microbeamformers 12a and 12b is directed by the transmit controller 18 coupled to the T/R switch, which receives input from the user's operation of the user interface or control panel 38 and controls the steering direction and focusing of beams to and from the array transducer in accordance with system control settings. The transmit controller can include configurable hardware, such as a microprocessor, or integrated circuit or other hardware chip-based device.

The partially beamformed signals produced by the microbeamformers 12a, 12b are coupled to a main beamformer 20 where partially beamformed signals from the individual patches of elements are combined into a fully beamformed signal. For example, the main beamformer 20 may have 128 channels, each of which receives a partially beamformed signal from a patch of 12 transducer elements. In this way the signals received by over 1500 transducer elements of a two dimensional array can contribute efficiently to a single beamformed signal. In an example where, for example, 128 transducer elements are used in the array, then the elements can be coupled directly to main beamformer 20 without use of any microbeamformers.

The beamformed signals are coupled to a fundamental/harmonic signal separator 22. The separator 22 acts to separate linear and nonlinear signals so as to enable the identification of the strongly nonlinear echo signals returned from VARs. The separator 22 may operate in a variety of ways such as by bandpass filtering the received signals in fundamental frequency and harmonic frequency bands, or by a process known as pulse inversion harmonic separation. A suitable fundamental/harmonic signal separator is shown and described in international patent publication WO 2005/074805 (Bruce et al.) The separated signals are coupled to a signal processor 24 where they may undergo additional enhancement such as speckle removal, signal compounding, and noise elimination.

The processed signals are coupled to a B mode processor 26 and a Doppler processor 28. The B mode processor 26 employs amplitude detection for the imaging of structures in the body such as muscle, tissue, and blood vessels. B mode images of structure of the body may be formed in either the harmonic mode or the fundamental mode. Tissues in the body and VARs both return both types of signals and the harmonic returns of VARs enable VARs to be clearly segmented in an image. The Doppler processor processes temporally distinct signals from moving tissue and blood flow for the detection of motion of substances in the image field including VARs. The structural and motion signals produced by these processors are coupled to a scan converter 32 and a volume renderer 34, which produce image data of tissue structure, flow, or a combined image of both characteristics. The scan converter will convert echo signals with polar coordinates into image signals of the desired image format such as a sector image in Cartesian coordinates. The volume renderer 34 will convert a 3D data set into a projected 3D image as viewed from a given reference point as described in U.S. Pat. No. 6,530,885 (Entrekin et al.) As described therein, when the reference point of the rendering is changed the 3D image can appear to rotate in what is known as kinetic parallax. This image manipulation is controlled by the user as indicated by the Display Control line between the user interface 38 and the volume renderer 34. Also described is the representation of a 3D volume by planar images of different image planes, a technique known as multiplanar reformatting. The volume renderer 34 can operate on image data in either rectilinear or polar coordinates as described in U.S. Pat. No. 6,723,050 (Dow et al.) The 2D or 3D images are coupled from the scan converter and volume renderer to an image processor 30 for further enhancement, buffering and temporary storage for display on an image display 40.

A graphics processor 36 is also coupled to the image processor 30 which generates graphic overlays for displaying with the ultrasound images. These graphic overlays can contain standard identifying information such as patient name, date and time of the image, imaging parameters, and the like, and can also produce a graphic overlay of a beam vector steered by the user as described below. For this purpose the graphics processor receives input from the user interface 38. The user interface is also coupled to the transmit controller 18 to control the generation of ultrasound signals from the transducer arrays 10a and 10b and hence the images produced by and therapy applied by the transducer arrays. The transmit parameters controlled in response to user adjustment include the MI (Mechanical Index) which controls the peak pressure of the transmitted waves, which is related to cavitational effects of the ultrasound, steering of the transmitted beams for image positioning and/or positioning (steering) of a therapy beam.

The transducer arrays 10a and 10b transmit ultrasonic waves into the cranium of a patient from opposite sides of the head, although other locations may also or alternately be employed such as the front of the head or the sub-occipital acoustic window at the back of the skull. The sides of the head of most patients advantageously provide suitable acoustic windows for transcranial ultrasound at the temporal bones around and above the ears on either side of the head. In contrast to other ultrasonic treatments applied of different body parts, access areas providing suitable acoustic windows in the skull may be limited. The present invention advantageously allows reducing the instantaneous acoustic power at the skin's surface, thereby providing an improved patient's safety. In order to transmit and receive echoes through these acoustic windows the transducer arrays must be in good acoustic contact at these locations which may be done by holding the transducer arrays against the head with a headset. For instance, FIG. 2a shows a headset 62 for two matrix array probes 10 mounted on the head 60 of a mannequin. The sides of the head of most patients advantageously provide suitable acoustic windows for transcranial ultrasound at the temporal bones around and in front of the ears on either side of the head. In order to transmit and receive echoes through these acoustic windows the transducer arrays must be in good acoustic contact at these locations which may be done by holding the transducer arrays against the head with the headset 62. A headset may have a snap-on deformable acoustic standoff 44 which allows the transducer array to be manipulated by its conformal contact surface and aimed at the arteries within the brain while maintaining acoustic contact against the temporal window. The illustrated probe 10 is curved by bending the probe handle by 90°, which makes the probe more stable when attached to the headset 62, as its center of gravity is closer to the head and headset. The acoustic coupling objective is facilitated by integrating a mating spherical surface into the probe handle, which allows the probe to pivot in the headset 62 until it is strongly and tightly coupled to the temporal window of the patient.

Figure 2:
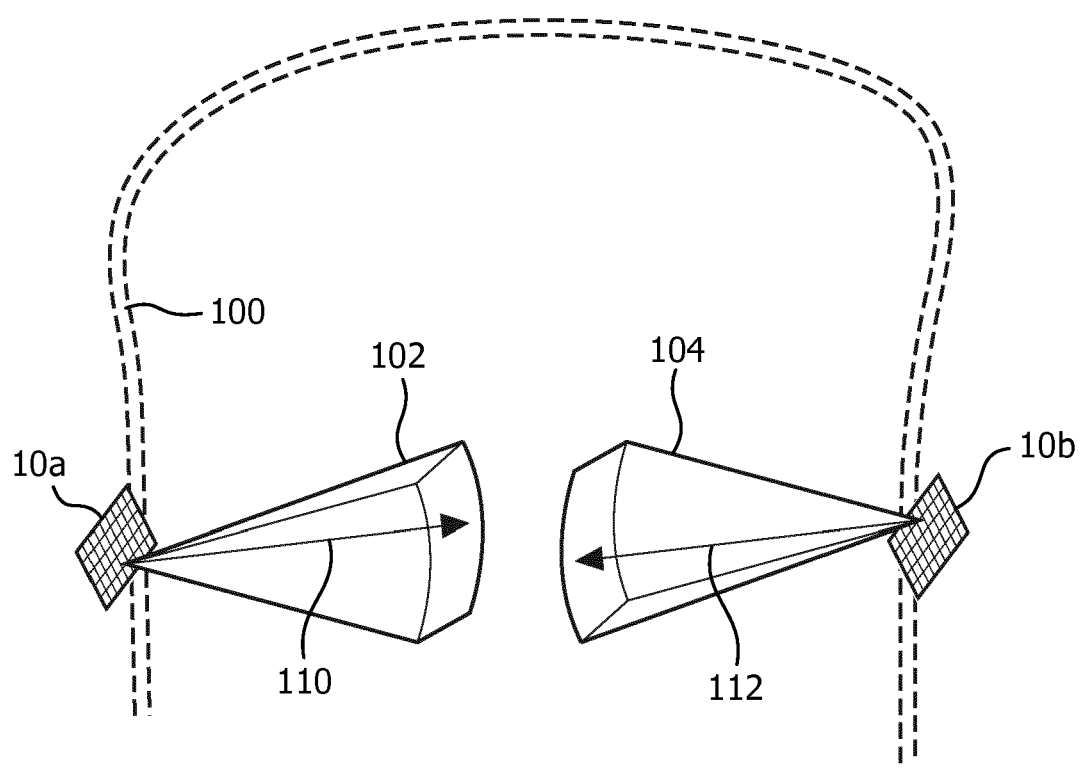
FIG. 2 illustrates regions of the cranium which can be treated by transducer arrays located over the temporal bone on either side of the head.
Figure 2A:
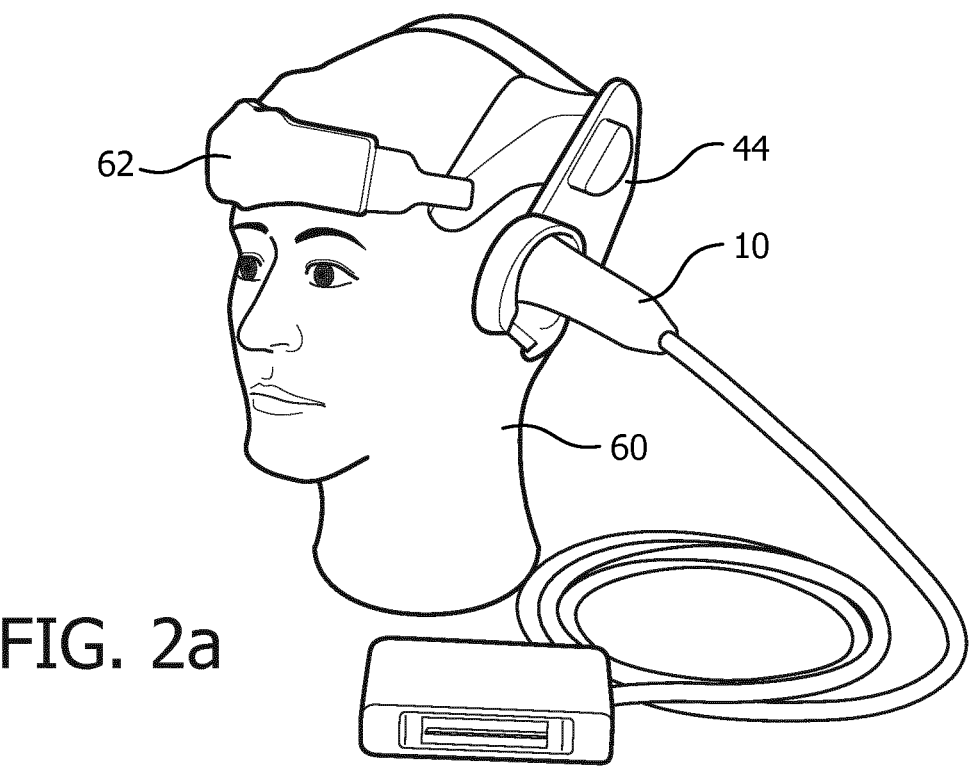
FIG. 2a illustrates a cranial headset suitable for holding transducer arrays in acoustic contact with the temporal bone regions of the head.

FIG. 2 illustrates the volumetric image fields 102, 104 scanned by matrix array transducers 10a and 10b when acoustically coupled to scan through the skull 100. A clinician can image the cranial vasculature in these volumetric image fields and steer the pyramidal image fields in different directions to search for blood clots obstructing the cranial blood flow. At each position of the image field 102, 104 the clinician can look for obstructions of the blood flow in the real time images on the display, or can capture (freeze) an image or map of the cranial vasculature. When the vascular map is acquired and held statically, the image can undergo enhanced processing (e.g., compounding, signal averaging) to improve the resolution or scale of the image, and can be manipulated on the screen and examined carefully at different points and from different views in a precise search for blood vessel occlusions. In this way the clinician can diagnose for stenoses. If the clinician examines a vascular map and finds no evidence of obstruction in the blood flow paths, the clinician can steer the image field to another region of the cranium and examine the vascular map of another image field. The clinician can use the Doppler data of the vascular map or the spectral Doppler function of the ultrasound system to take flow velocity measurements at specific points in the cranial vasculature, then use the report generation capabilities of the ultrasound system to record the measurements and prepare a report of his diagnosis.

If the clinician discovers a stenosis, therapy can be offered by applying the method of the invention VARs at the site of the stenosis in an effort to dissolve the blood clot with the ultrasound beam. The clinician activates the "therapy" mode of the ultrasound system, and a graphic 110, 112 appears in the image field 102, 104, depicting the vector path of a therapeutic ultrasound beam. The therapeutic ultrasound beam is manipulated by a control on the user interface 38 until the vector graphic 110 or 112 is focused at the site of the blood clot. In the implementations of the present disclosure described below, the therapy beam is automatically scanned in patterns at and around the blood clot at which the clinician has aimed the vector graphic. The therapeutic beam can be a tightly focused, convergent beam or a beam with a relatively long focal length known as a pencil beam. The energy produced for the therapeutic beam can be in excess of the ultrasound levels permitted for diagnostic ultrasound, in which case the VARs at the site of the blood clot will be effectively destroyed. While not willing to be bound to any particular scientific theory, it may be supposed that the energy of the resulting VARs ruptures will effectively act on the blood clot, tending to break up the clot and dissolve it in the bloodstream. However in some instances insonification of the VARs at diagnostic energy levels may be sufficient to dissolve the clot.

Figure 3:
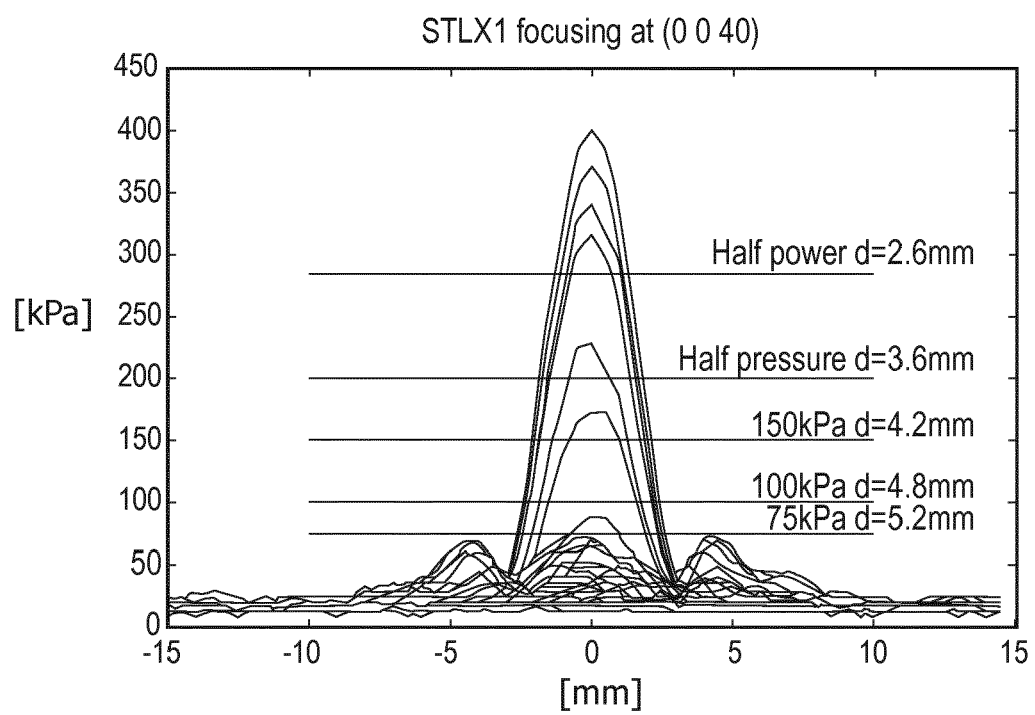
FIG. 3 is a graphic illustration of the pressure thresholds of a typical ultrasound beam.
Figure 4A:
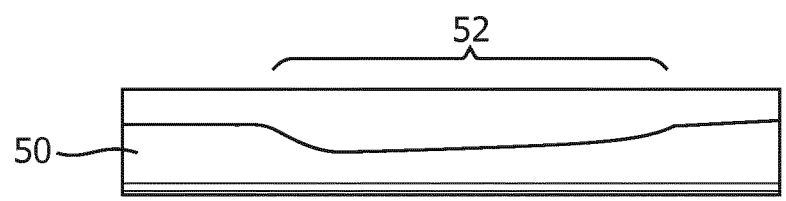
FIGS. 4a, 4b, and 4c are cross-sectional illustrations of blood clots following different applications of different sequences of ultrasonic therapy beams.
Figure 4B:
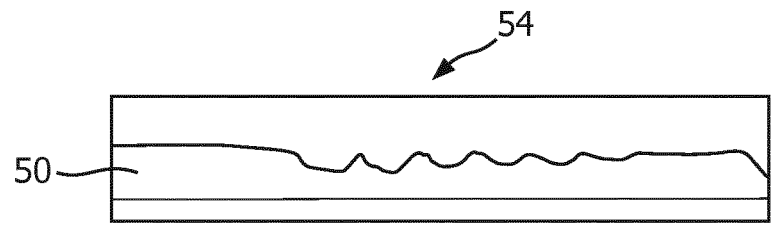
Figure 4C:
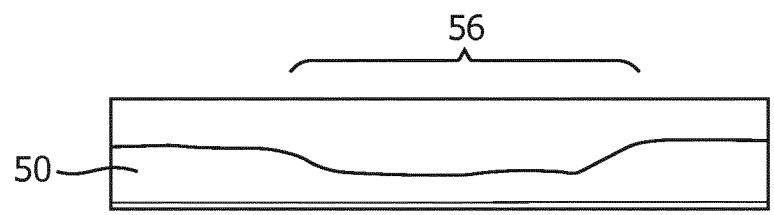

FIG. 3 is a plot of the pressure level profile of the cross-section of a typical focused ultrasound therapy beam area used for sonothrombolysis. The lines of the plot show focused beam diameters at various pressure levels. VARs, and particularly microbubbles, in the ultrasound field are destroyed rapidly by relatively modest pressures of 50-100 kPa, but will remain therapeutically active for sonothrombolysis, typically for several tens of milliseconds, as long as they continue to remain in the ultrasound field. However, when the beam is of sufficient amplitude to have a therapeutic effect, typically a peak pressure of 200-400 kPa, VARs in proximity to the beam will be destroyed by the reduced amplitude at the sides of the beam without contributing to the therapeutic effect. Because of this effect, several undesired results are possible when steering an ultrasound beam to cover a larger treatment volume around a blood clot. If the beams are steered to be spaced too closely together, the therapeutic effect from successive beams will be reduced. This is illustrated by the picture of the blood clot shown in FIG. 4a which shows a length of an in vitro blood clot 50 which has been lysed by a therapy beam pattern made of a succession of therapy beams transmitted from left to right along the top of the blood clot as indicated at 52. As the picture shows, the initial therapy beams of the pattern are effective to deeply break up the clot on the left side, but the depletion of microbubbles due to unwanted microbubbles destruction, in proximity of the initial therapy beams, has left fewer effective microbubbles as the scanning proceeds to the right. The result is seen to be only a shallow depth of clot lysis on the right side of the bracketed area. However, if the individual beams are spaced too far enough apart to avoid this effect, the result is an inadequate clot exposure to the therapy beams, resulting in clot scalloping, as shown in FIG. 4b at 54. The system and method of the present disclosure are effective to prevent both of these unwanted results, as shown in FIG. 4c at 56.

In accordance with the principles of the present disclosure, a number of unique therapy beam scan formats are described which avoid this kind of scalloping and treatment effect reduction due to the premature/undesired destruction of VARs during sonothrombolysis. These scan formats consist of the sequential use of two or more unique scan patterns with focused ultrasound beam spacing that is typically wide enough to limit undesirable microbubble destruction Transmission of the therapy beams is interleaved in time to still yield global and uniform clot coverage, with a sufficiently long VAR replenishment time between each scan pattern to ensure the presence of a large enough VAR concentration required for effective therapy delivery. Each scan pattern has a focused ultrasound beam spacing that is typically wide enough to limit unwanted VAR destruction. Our research has indicated that the beam spacing should, for a 400 kPa peak pressure beam, preferably be at least as large as the half-power beam width (corresponding to about 70% of maximum beam pressure), ideally on the order of the 100 kPa to half-pressure beam width, but no larger than the 75-100 kPa (18.75% to 25%) pressure beam width (see FIG. 3). For a typical focused sonothrombolysis therapy ultrasound beam at 1 MHz set to insonify the VARs, particularly microbubbles, at its focal zone at 400 kPa, this beam spacing would be approximately in the range of 2.6 mm (size of half-power beam width) to 3.6 mm (size of half-pressure beam width) or to 5.2 mm.

A beam scan pattern suitable for use in accordance with the present disclosure consists of a collection of individual focused beams, transmitted in a sequential manner to cover the entire clot volume and surrounding tissue, thereby ensuring an adequate treatment margin. Typical cerebral blood clots are cylindrical in shape, with a diameter corresponding to the inside diameter of the occluded vessel, 2-5 mm in the case of the middle cerebral artery, and up to several centimeters in length. In order to achieve thorough insonification of the clot and its surrounding tissue, each scan pattern preferably covers a typical cross-sectional area of 1-5 $cm^2$. This means that each scan pattern is composed of many beams, given a desired beam spacing and target region coverage. To further minimize beam overlap and resulting VAR destruction from adjacent beams, the beams of each successive scan pattern are positioned in between those of the preceding pattern, in an interleaved manner. A variety of beam pattern sequences can be used, such as two beam, three beam, four beam, or five beam sequences. All the beam patterns in the sequence can be different or some of the beam patterns can be the same.

Figure 5D:
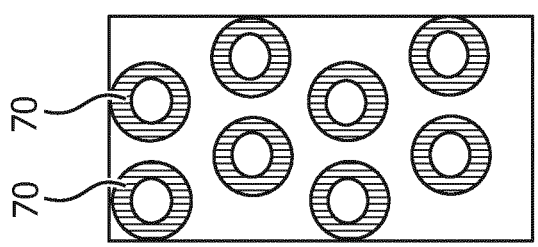
FIGS. 5a to 5d illustrate four ultrasonic therapy beam patterns in accordance with the principles of the present disclosure.
Figure 5C:
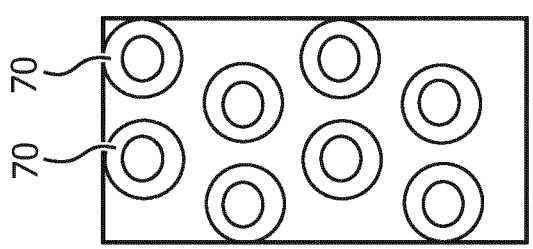
Figure 5E:
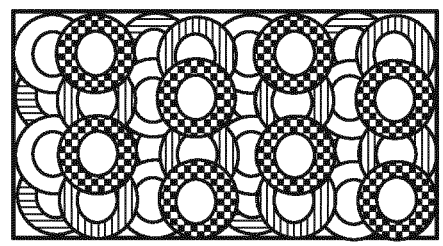
FIG. 5e illustrates the superposition of the four patterns of FIGS. 5a to 5d.
Figure 5B:
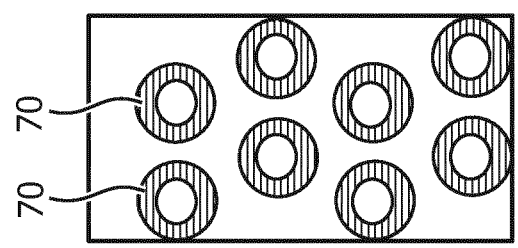
Figure 5A:
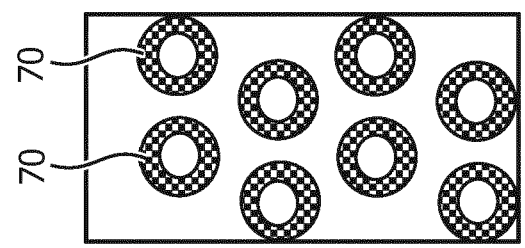

FIGS. 5a and 5b illustrate two example beam patterns transmitted in an example beam pattern sequence. These drawings represent the beams 70 as viewed axially in cross-section at the blood clot location, with the outer circle demarcating the half pressure beam profile and the smaller circle the peak pressure beam axis. The relative position of the beams and the beamwidth of the beams can be tuned to reduce the effect on interfering with contrast agent present in adjacent beams. For example, the outer circles of the beams in FIGS. 5a and 5b are not overlapping, and are spaced so as to limit adjacent beams from rupturing VARs or microbubbles outside of the beam focus region. A variety of beam patterns can also be used. For example, an X-by-Y matrix of beams can be used, and different numbers of beams can be selected as well. In some embodiments, the number of beams used, e.g., can range from 5 to 50, 10 to 30, or 10 to 20. In FIGS. 5a to 5d, each beam pattern consists of eight individually transmitted and focused beams arranged in the four by three matrix, which in this example covers a cross-sectional area of about one square centimeter. The center-to-center beam spacing in this example is 2.6 mm. It can be seen that the beams of the scan patterns of FIGS. 5a to 5d are spatially interleaved, so that one scan pattern will fill in the spaces between the other scan pattern.

The scan patterns of FIGS. 5a to 5d are transmitted in a four-pattern sequence, if desired with replenishment periods or time intervals between the transmitted beam patterns. The region of the clot is first scanned with the beams in the pattern of FIG. 5a, followed by scanning with the beams of FIG. 5b, which are offset to the left from the pattern of FIG. 5a by half of the interbeam spacing (e.g., 1.3 mm). Then the beam pattern of FIG. 5a is transmitted again but offset vertically from the beam pattern of FIG. 5a by half of the interbeam spacing (e.g., 1.3 mm), followed by scanning with the beam pattern of FIG. 5b, also offset vertically from the beam pattern of FIG. 5b by half of the interbeam spacing. After each scan pattern is executed to insonify the targeted therapeutic volume, there is a pause of a few seconds (typically two seconds) to allow new VARs to replenish the therapeutic region, after which the next scan pattern is executed. Acoustically, the clot target is exposed to a substantially uniform ultrasound field after the completion of the four successive scan patterns, as illustrated in FIG. 5e.

FIG. 6 is a numerical example of another four-pass scanning sequence in accordance with the present disclosure. In this sequence the beams "1" of the first beam pattern, are spaced apart horizontally along the first, third, and fifth rows of the grid. The second beam pattern, represented by the grid locations "2", are spaced apart horizontally in the second and fourth rows and are diagonally located between the beams of the first pattern. The beams "3" of the third pattern fill in the spaces in the first, third, and fifth rows which were not scanned by the beams of the first pattern and also fill in vertically between the beams of the second beam pattern. The beams "4" of the fourth beam pattern are seen to fill in vertically between the beams of the first beam pattern and horizontally between the beams of the second beam pattern. The result is a full insonification of the grid area and hence the volume traversed by the beams. FIG. 4c is a picture of the desired uniform clot lysis profile resulting from clot lysis with the beam patterns of FIG. 6.

A three-pass scanning sequence of the same grid and volume as FIG. 6 is illustrated in FIG. 7. Beams "1" of the first beam pattern are transmitted in alternating alignment, separated by two grid locations horizontally and one grid location vertically. The beams "2" of the second beam pattern are similarly transmitted in a pattern offset from the first beam pattern, separated by two grid locations horizontally and one grid location vertically. The beams "3" of the third grid pattern are offset in a pattern different from those of the first and second beam patterns and fill in the remaining locations in the grid, again separated from each other by two grid locations horizontally and one grid location vertically. This three-pass beam pattern sequence is also seen to fully insonify the grid area, but spacing the beams of each pattern to avoid undesired adjacent VAR destruction so that these VARs can be effectively therapeutically destroyed by a subsequent beam pattern. As with the previous examples, a refresh time is allowed between successive patterns to allow the inflow of fresh VARs to the blood clot location.

FIG. 8 shows another example of a beam pattern that can be used in the present disclosure. A four beam scan sequence is shown such that the beams identified as "1" can be scanned first. Following a wait time, such as two seconds, beams identified as "2" can be scanned, then beams identified as "3", and beams identified as "4".

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the disclosure. The computer program instructions can be stored on any suitable computer-readable hardware medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

Vascular acoustic resonators useful in the method according to the invention include any component capable of converting acoustic pressure in a propagation-medium into micron-size displacements, capable of applying strain onto blood clots or vessel walls, also with micron-size deformation amplitude. Preferred examples of suitable VARs include gas-filled microvesicles, i.e. vesicles of nano- or micron-size comprising a stabilizing envelope containing a suitable gas therein. The formulation and preparation of VARs is well known to those skilled in the art, including, for instance, formulation and preparation of: microbubbles with an envelope comprising a phospholipid, as described e.g. in WO 91/15244, U.S. Pat. No. 5,686,060 (Schneider et al.) and WO 2004/069284; microballoons with an envelope comprising a polymer, as described e.g. in U.S. Pat. No. 5,711,933; or microcapsules with an envelope comprising a biodegradable water insoluble lipid, as described e.g. in U.S. Pat. No. 6,333,021. Preferably, the stabilizing envelope comprises an amphiphilic material, more preferably a phospholipid. Preferred phospholipids include esters of glycerol with one or preferably two (equal or different) residues of fatty acids and with phosphoric acid, wherein the phosphoric acid residue is in turn bound to a hydrophilic group. Other preferred phospholipids include phosphatidic acids, i.e. the diesters of glycerol-phosphoric acid with fatty acids. Particularly preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin. Polymer-modified phospholipids, including pegylated phospholipids, can also be advantageously employed for forming the stabilizing envelope of microbubbles. Any biocompatible gas, gas precursor or mixture thereof may be employed to fill the above microvesicles. Fluorinated gases are preferred, in particular perfluorinated gases. Particularly preferred gases are $SF_6$, $C_3F_8$, $C_4F_{10}$ or mixtures thereof, optionally in admixture with air, oxygen, nitrogen, carbon dioxide or mixtures thereof, as described for instance in U.S. Pat. Nos. 6,881,397 or 5,556,610.

The components forming the stabilizing envelope of the VARs, optionally in admixture with other excipients, can be stored as a dry residue in contact with the desired gas(es). Microvesicles are typically prepared by contacting the dry residue in the presence of the gas(es) with an aqueous carrier (e.g., saline or glucose solution) under gentle shaking, thus obtaining an aqueous suspension of microvesicles. The microvesicle suspension is then typically administered by injection, preferably intravenously.

FIGS. 9a to 9b show experimental results conducted on rats. The figures illustrate contrast enhanced ultrasound images of micro-embolized rat hind limb containing vascular acoustic resonators and insonified with therapy beams in a plurality of sequential patterns for a treated group (b) and a control (untreated) group (a). In animals perfusion of rat hind limb was assessed at a baseline FIGS. 9(a1) and 9(b1) performing contrast enhanced ultrasound imaging (CEUS) using ultrasound clinical system (Sequoi512) plus ultrasound contrast agent (SonoVue®). The suspension of autologous microthrombi were injected in the femoral artery and a successful occlusion was assessed 10 min after performing CEUS. The successful occlusion was evidenced by the absence of the contrast enhancement in ultrasound images illustrated in FIGS. 9(a2) and 9(b2). Thirty minutes later no perfusion was visible in the control group represented by FIGS. 9(a3); whereas 30 minutes after the treatment with the ultrasound therapy beams combined with the VARs in the rat hind limb from the treated group reperfusion was evidenced as shown in FIG. 9(b3). The ultrasound beam pattern transmitted in the plurality of sequential patterns similar to that described in FIG. 5 comprised 12 individually transmitted and focused beams arranged in the four by three matrix. The center-to-center beam spacing used in these experiments was 2.6 mm and the maximal peak pressure was 400 kPa. Reperfusion was graded using a semi-quantitative grading (0: no reperfusion; 1: minimal; 2: partial; 3: complete).

The invention claimed is:

1. An ultrasound system for insonifying a region of interest containing vascular acoustic resonators (VARs) with spatially interleaved patterns of ultrasound beams comprising:
an ultrasound array arranged to transmit ultrasound therapy beams into the region of interest, the therapy beams having beam areas with a peak beam pressure which is sufficient to destroy VARs in the region of interest; and
a transmit controller coupled to the array and arranged to electronically control steering of the therapy beams in a plurality of sequential patterns of beams separated by a beam spacing which, in consideration of the peak beam pressure, leaves residual VARs between adjacent beams after beam transmission, wherein a subsequent in time pattern comprises beam areas which are spatially interleaved between beam areas of a previous pattern so as to destroy residual VARs.

2. The ultrasound system of claim 1, wherein the plurality of sequential patterns comprises a first pattern of ultrasound therapy beams being separated from each other by spaces according to a predetermined spacing, and
a second pattern of ultrasound therapy beams steered to the spaces separating the beams of the first beam pattern from each other.

3. The ultrasound system of claim 2, wherein the plurality of sequential patterns further comprises a third pattern of ultrasound therapy beams which are spatially interleaved between the beams of the first and second beam patterns.

4. The ultrasound system of claim 3, wherein the plurality of sequential patterns further comprises a fourth pattern of ultrasound therapy beams that are spatially interleaved between the beams of the first, second and third beam patterns.

5. The ultrasound system of claim 2, wherein the plurality of sequential patterns further comprises a third and fourth patterns of ultrasound therapy beams having the same beam patterns as the first and second beam patterns and offset by an interbeam spacing between the ultrasound therapy beams.

6. The ultrasound system of claim 5, wherein the plurality of sequential patterns further comprises a third beam pattern of the same pattern as the second beam pattern, and a fourth beam pattern of the same pattern as the first beam pattern, and the ultrasound therapy beams being offset by the interbeam spacing.

7. The ultrasound system of claim 1, wherein the transmit controller is further arranged to cause the system to refrain from transmitting over a time interval between transmission of two subsequent patterns.

8. The ultrasound system of claim 7, wherein the time interval is at least 0.1 seconds.

9. The ultrasound system of claim 8, wherein the time interval ranges from about one to two seconds.

10. The ultrasound system according to claim 1, wherein centers of the beam areas in any pattern of ultrasound therapy beams are separated from each other by a spacing at least equal to a half power beam width.

11. The ultrasound system of claim 10, wherein the centers of the beam areas are separated from each other by a spacing at least equal to a half pressure beam width.

12. The ultrasound system according to claim 10, wherein the centers of the beam areas in any pattern of ultrasound therapy beams are separated from each other by a spacing not greater than the 18.75% pressure beam width.

13. The ultrasound system according to claim 10, wherein the centers of the beams are separated from each other by a spacing not greater than the 25% pressure beam width.

14. The ultrasound system of claim 10, wherein the centers of the beam areas in any pattern of ultrasound therapy beams are separated from each other by a spacing ranging from 2.6 to 5.2 mm.

15. The ultrasound system of claim 1, wherein the plurality of sequential patterns comprises
a first pattern of ultrasound therapy beams in which beams are separated from each other horizontally and vertically;
a second pattern of ultrasound therapy beams in which beams are spatially interleaved horizontally and vertically between the beams of the first pattern; and
a third pattern of ultrasound therapy beams in which beams are spatially interleaved horizontally and vertically between the beams of the first and second patterns.

16. The ultrasound system of claim 15, wherein the plurality of sequential patterns further comprises:
a fourth pattern of ultrasound therapy beams in which beams are spatially interleaved horizontally and vertically between the beams of the first, second and third patterns.

* * * * *